US008374698B2

(12) United States Patent
Ok et al.

(10) Patent No.: US 8,374,698 B2
(45) Date of Patent: Feb. 12, 2013

(54) PACKAGE FOR AN IMPLANTABLE NEURAL STIMULATION DEVICE

(75) Inventors: Jerry Ok, Canyon Country, CA (US); Robert J. Greenberg, Los Angeles, CA (US); Neil Hamilton Talbot, Crescenta, CA (US); James Singleton Little, Saugus, CA (US); Rongqing Dai, Valencia, CA (US); Jordan Matthew Neysmith, Pasadena, CA (US); Kelly H. McClure, Simi Valley, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 11/893,939

(22) Filed: Aug. 18, 2007

(65) Prior Publication Data

US 2008/0058895 A1   Mar. 6, 2008

Related U.S. Application Data

(60) Provisional application No. 60/838,714, filed on Aug. 18, 2006, provisional application No. 60/880,994, filed on Jan. 18, 2007.

(51) Int. Cl.
*A61N 1/375* (2006.01)
(52) U.S. Cl. .......................................................... 607/54
(58) Field of Classification Search .................... 607/54, 607/2
See application file for complete search history.

(56) References Cited

U.S. PATENT DOCUMENTS

| | | | |
|---|---|---|---|
| 3,699,970 A | 10/1972 | Brindley et al. | |
| 4,573,481 A | 3/1986 | Bullara | |
| 4,837,049 A | 6/1989 | Byers et al. | |
| 5,006,286 A | 4/1991 | Dery et al. | |
| 5,109,844 A | 5/1992 | de Juan, Jr. et al. | |
| 5,215,088 A | 6/1993 | Normann et al. | |
| 5,468,936 A | 11/1995 | Deevi et al. | |
| 5,611,140 A | 3/1997 | Kulesza et al. | |
| 5,935,155 A | 8/1999 | Humayun et al. | |
| 5,954,751 A * | 9/1999 | Chen et al. | 607/5 |
| 6,014,586 A * | 1/2000 | Weinberg et al. | 607/36 |
| 6,258,626 B1 * | 7/2001 | Wang et al. | 438/107 |
| 6,361,716 B1 | 3/2002 | Kleyer et al. | |
| 6,400,989 B1 | 6/2002 | Eckmiller | |
| 6,414,884 B1 * | 7/2002 | DeFelice et al. | 365/195 |
| 6,458,157 B1 | 10/2002 | Suaning | |
| 6,940,158 B2 * | 9/2005 | Haba et al. | 257/686 |

(Continued)

FOREIGN PATENT DOCUMENTS

WO   WO 2006/118679   11/2006
WO   WO 2007/035774   3/2007

OTHER PUBLICATIONS

Hansjoerg Beutel, et al.; Versatile 'Microflex'—Based Interconnection Technique; Part of SPIE Conference on Smart Electronics & MEMS; Mar. 1998; pp. 174-182; San Diego, CA.

(Continued)

*Primary Examiner* — Carl H Layno
*Assistant Examiner* — Jeremiah Kimball
(74) *Attorney, Agent, or Firm* — Scott B. Dunbar

(57) ABSTRACT

The present invention is an improved hermetic package for implantation in the human body. The implantable device includes an electrically non-conductive substrate with electrically conductive vias. A flip-chip circuit is attached to the substrate using conductive bumps and electrically connected to a first subset of the vias. The flip-chip circuit can contain one or more stacks or a folded stack. A wire-bonded circuit is also attached to the substrate and electrically connected to a second subset of the vias. A cover is bonded to the substrate. The cover, substrate, and vias form an improved hermetic package for implantation.

13 Claims, 12 Drawing Sheets

U.S. PATENT DOCUMENTS

| | | | |
|---|---|---|---|
| 7,132,173 B2 * | 11/2006 | Daulton | 428/621 |
| 2002/0026108 A1 * | 2/2002 | Colvin, Jr. | 600/316 |
| 2002/0038134 A1 * | 3/2002 | Greenberg et al. | 607/1 |
| 2002/0091421 A1 * | 7/2002 | Greenberg et al. | 607/54 |
| 2002/0139556 A1 * | 10/2002 | Ok et al. | 174/50.6 |
| 2002/0193845 A1 * | 12/2002 | Greenberg et al. | 607/54 |
| 2003/0048621 A1 | 3/2003 | Blood et al. | |
| 2003/0233134 A1 * | 12/2003 | Greenberg et al. | 607/36 |
| 2005/0228467 A1 | 10/2005 | Jiang | |
| 2006/0103005 A1 * | 5/2006 | Schulz-Harder et al. | 257/703 |
| 2006/0108676 A1 * | 5/2006 | Punzalan et al. | 257/686 |
| 2006/0172462 A1 * | 8/2006 | Karnezos | 438/109 |
| 2006/0173511 A1 | 8/2006 | Greenberg et al. | |
| 2006/0247734 A1 | 11/2006 | Greenberg et al. | |
| 2007/0041164 A1 * | 2/2007 | Greenberg et al. | 361/752 |
| 2008/0046021 A1 * | 2/2008 | Greenberg et al. | 607/36 |
| 2008/0058895 A1 * | 3/2008 | Ok et al. | 607/54 |

OTHER PUBLICATIONS

L. Del Castillo, et al.; Flip Chip Packaging of a MEMS Neuro-Prosthetic System; Proc. IMAPS Int. Conf. & Exh. on Adv. Packaging & Systems; Mar. 2002, 6 pages; Reno NV.

M. Pourbaix, et al.; Atlas of Electrochemical Equilibria; National Association of Corrosion Engineers, 1974, 9 pages; Houston, TX.

* cited by examiner

PACKAGE FOR AN IMPLANTABLE NEURAL STIMULATION DEVICE

CROSS-REFERENCE TO RELATED APPLICATIONS

This application claims benefit of U.S. Provisional Patent application Ser. No. 60/838,714, filed on Aug. 18, 2006, entitled "Package for an Implantable Neural Stimulation Device" and of U.S. Provisional Patent application Ser. No. 60/880,994, filed on Jan. 18, 2007, entitled "Package for an Implantable Neural Stimulation Device" the disclosures of both are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved hermetic package for an implantable neural stimulation device.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 µm. J. Opthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

US Patent Application 2003/0109903 to Peter G. Berrang describes a Low profile subcutaneous enclosure, in particular and metal over ceramic hermetic package for implantation under the skin.

U.S. Pat. No. 6,718,209, US Patent Applications Nos. 2002/0095193 and 2002/0139556 and US Patent Applications Nos. 2003/0233133 and 2003/0233134 describe inter alia package for an implantable neural stimulation device. Further descriptions of package for an implantable neural stimulation device can be found inter alia in U.S. Pat. No. 7,228,181; and US Patent Applications Nos. 20050288733 and 20060247754, all of which are assigned to a common assignee and incorporated herein by reference.

BRIEF SUMMARY OF THE INVENTION

The present invention is an improved hermetic package for implantation in the human body. The implantable device of the present invention includes an electrically non-conductive substrate including electrically conductive vias through the substrate. A circuit is flip-chip bonded to a subset of the vias. A second circuit is wire bonded to another subset of the vias. Finally, a cover is bonded to the substrate such that the cover, substrate and vias form a hermetic package.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention is an improved hermetic package for implanting electronics within a body. Electronics are commonly implanted in the body for neural stimulation and other purposes. The improved package allows for miniaturization of the package which is particularly useful in a retinal or other visual prosthesis for electrical stimulation of the retina.

Figure 1:
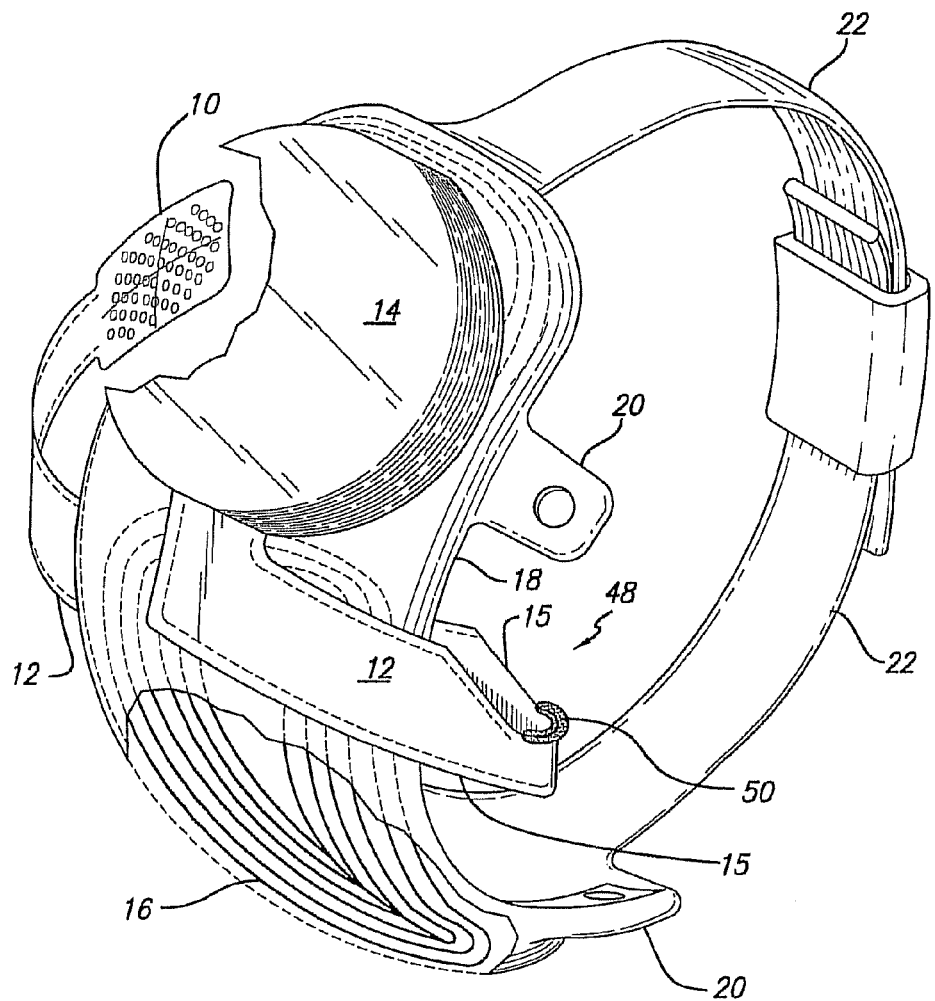
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera in the pars plana region, and is electrically coupled to an electronics package 14, external to the sclera. Further an electrode array fan tail 15 is formed of molded silicone and attaches the electrode array cable 12 to a molded body 18 to reduce possible damage from any stresses applied during implantation.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. This is beneficial as it reduces the height the entire device rises above the sciera. The design of the electronic package (described below) along with a molded body 18 which holds the secondary inductive coil 16 and electronics package 14 in the end to end orientation minimizes the thickness or height above the sclera of the entire device. This is important to minimize any obstruction of natural eye movement.

The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped secondary inductive coil 16.

Further it is advantageous to provide a sleeve or coating 50 that promotes healing of the scleratomy. Polymers such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicon, GORETEX®, or similar material would bond with scleral tissue and promote healing. In particular, a porous material will allow scleral tissue to grow into the pores promoting a good bond.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 2:
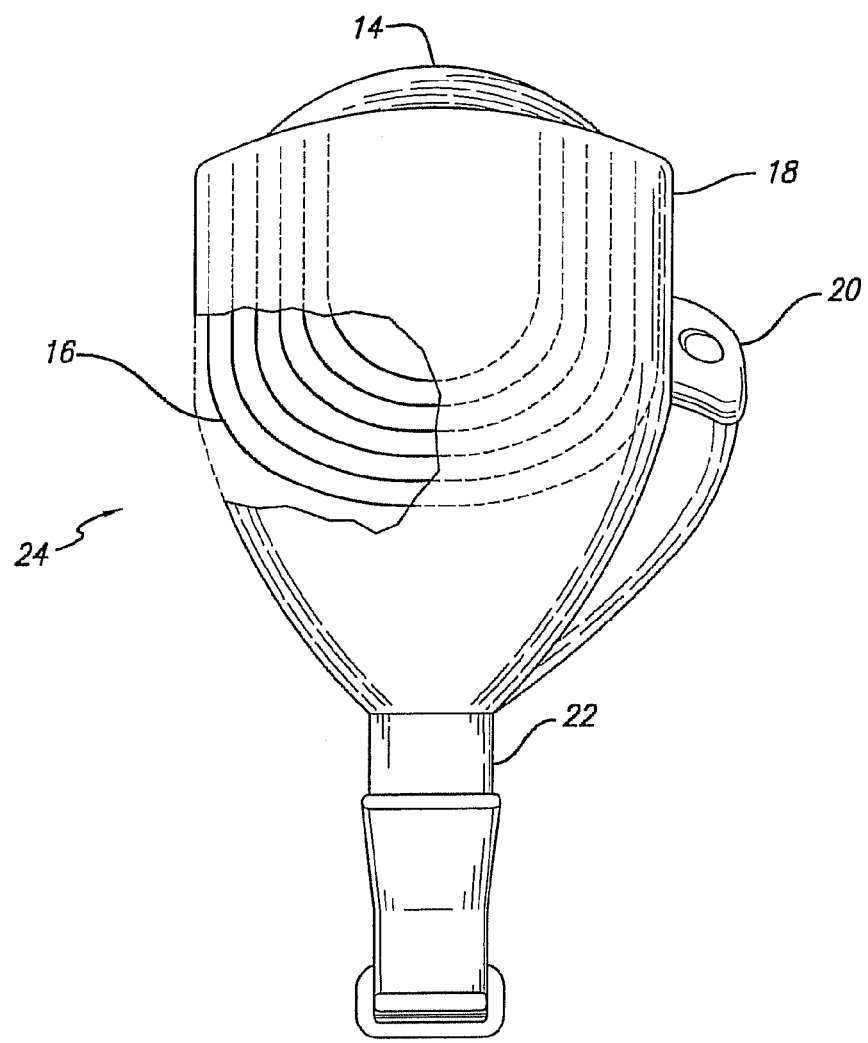
FIG. 2 is a side view of the implanted portion of the preferred retinal prosthesis showing the strap fan tail in more detail.

FIG. 2 shows side view of the implanted portion of the retinal prosthesis, in particular, emphasizing the strap fan tail 24. When implanting the retinal prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the retinal prosthesis is very delicate. It is easy to tear the molded body 18 or break wires in the secondary inductive coil 16 or electrode array cable 12. In order to allow the molded body 18 to slide smoothly under the lateral rectus muscle, the molded body 18 is shaped in the form of a strap fan tail 24 on the end opposite the electronics package 14.

Figure 3:
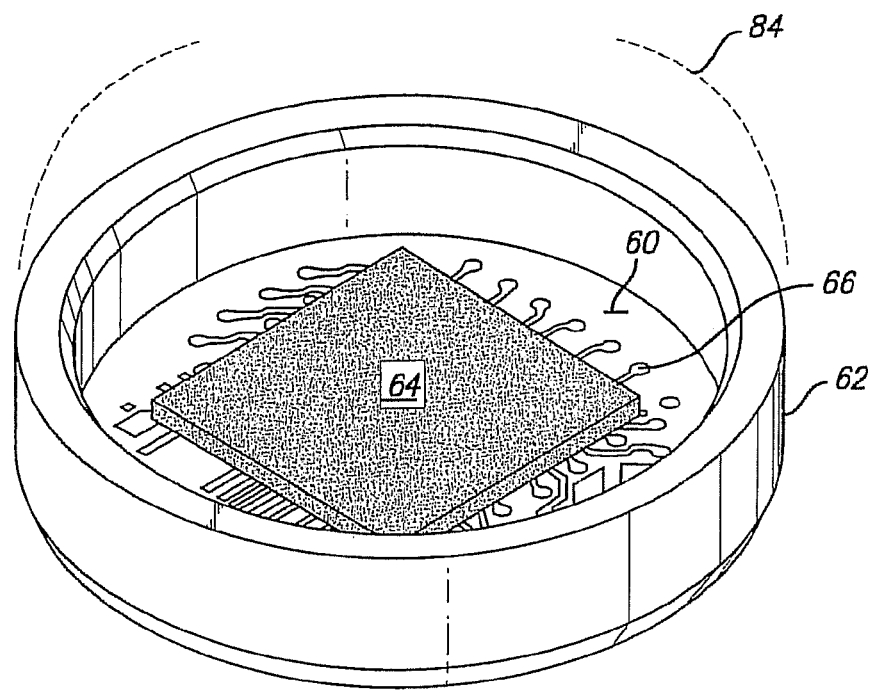
FIG. 3 is a perspective view of a partially built package showing the substrate, chip and the package wall.

FIG. 3 shows the hermetic electronics package 14 is composed of a ceramic substrate 60 brazed to a metal case wall 62 which is enclosed by a laser welded metal lid 84. The metal of the wall 62 and metal lid 84 may be any biocompatible metal such as Titanium, niobium, platinum, iridium, palladium or combinations of such metals. The ceramic substrate is preferably alumina but may include other ceramics such as zirconia. The ceramic substrate 60 includes vias (not shown) made from biocompatible metal and a ceramic binder using thick-film techniques. The biocompatible metal and ceramic binder is preferably platinum flakes in a ceramic paste or frit which is the ceramic used to make the substrate. After the vias have been filled, the substrate 60 is fired and lapped to thickness. The firing process causes the ceramic to vitrify biding the ceramic of the substrate with the ceramic of the paste forming a hermetic bond. Thin-film metallization 66 is applied to both the inside and outside surfaces of the ceramic substrate 60 and an ASIC (Application Specific Integrated Circuit) integrated circuit chip 64 is bonded to the thin film metallization on the inside of the ceramic substrate 60.

The inside thin film metallization 66 includes a gold layer to allow electrical connection using wire bonding. The inside film metallization includes preferably two to three layers with a preferred gold top layer. The next layer to the ceramic is a titanium or tantalum or mixture or alloy thereof. The next layer is preferably palladium or platinum layer or an alloy thereof. All these metals are biocompatible. The preferred metallization includes a titanium, palladium and gold layer. Gold is a preferred top layer because it is corrosion resistant and can be cold bonded with gold wire.

The outside thin film metallization includes a titanium adhesion layer and a platinum layer for connection to platinum electrode array traces. Platinum can be substituted by palladium or palladium/platinum alloy. If gold-gold wire bonding is desired a gold top layer is applied.

The package wall 62 is brazed to the ceramic substrate 60 in a vacuum furnace using a biocompatible braze material in the braze joint. Preferably, the braze material is a nickel titanium alloy. The braze temperature is approximately 1000° Celsius. Therefore the vias and thin film metallization 66 must be selected to withstand this temperature. Also, the electronics must be installed after brazing. The chip 64 is installed inside the package using thermocompression flip-chip technology. The chip is underfilled with epoxy to avoid connection failures due to thermal mismatch or vibration.

Figure 4:
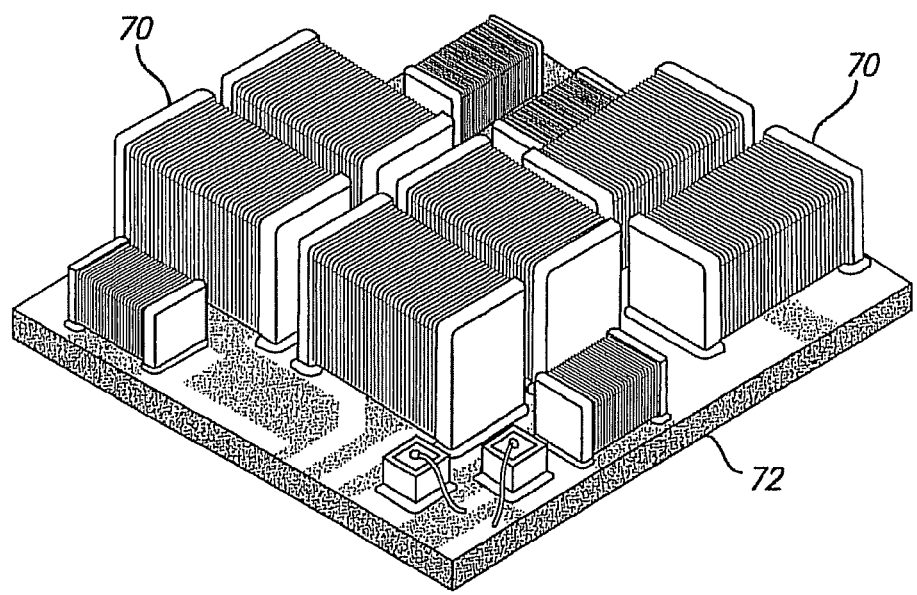
FIG. 4 is a perspective view of the hybrid stack placed on top of the chip.
Figure 5:
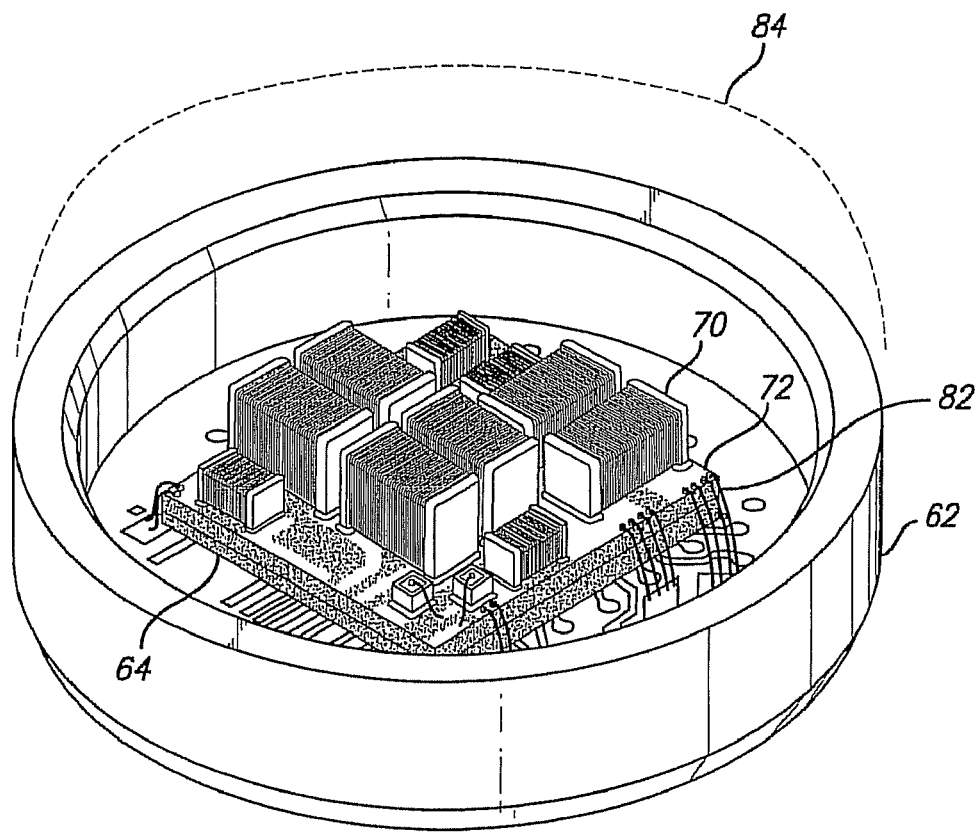
FIG. 5 is a perspective view of the partially built package showing the hybrid stack placed inside.

FIGS. 4 and 5 show off-chip electrical components 70, which may include capacitors, diodes, resistors or inductors (passives), are installed on a stack substrate 72 attached to the back of the chip 64, and connections between the stack substrate 72 and ceramic substrate 60 are made using gold wire bonds 82. The stack substrate 72 is attached to the chip 64 with non-conductive epoxy, and the passives 70 are attached to the stack substrate 72 with conductive epoxy.

Figure 6:
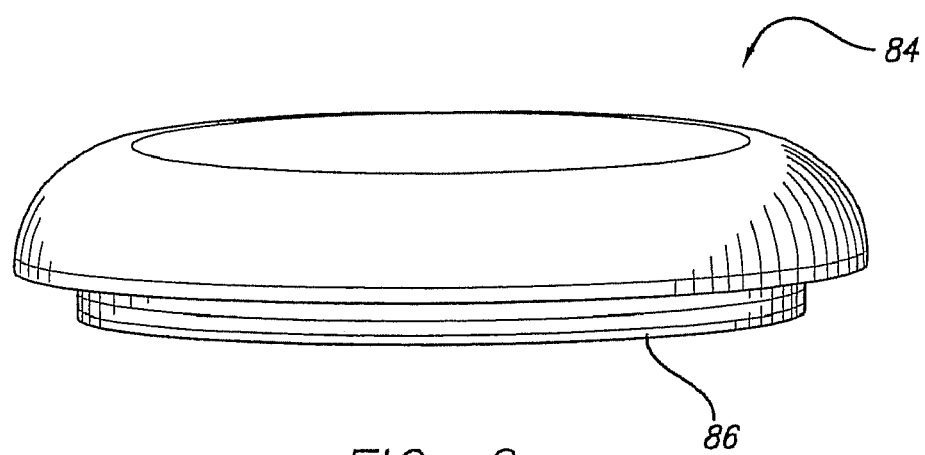
FIG. 6 is a perspective view of the lid to be welded to the top of the package.

FIG. 6 shows the electronics package 14 is enclosed by a metal lid 84 that, after a vacuum bake-out to remove volatiles and moisture, is attached using laser welding. A getter (moisture absorbent material) may be added after vacuum bake-out and before laser welding of the metal lid 84. The metal lid 84 further has a metal lip 86 to protect components from the welding process and further insure a good hermetic seal. The entire package is hermetically encased. Hermeticity of the vias, braze, and the entire package is verified throughout the manufacturing process. The cylindrical package was designed to have a low profile to minimize its impact on the eye when implanted.

The implant secondary inductive coil 16, which provides a means of establishing the inductive link between the external video processor (not shown) and the implanted device, preferably consists of gold wire. The wire is insulated with a layer of silicone. The secondary inductive coil 16 is oval shaped. The conductive wires are wound in defined pitches and curvature shape to satisfy both the electrical functional requirements and the surgical constraints. The secondary inductive coil 16, together with the tuning capacitors in the chip 64, forms a parallel resonant tank that is tuned at the carrier frequency to receive both power and data.

Figure 7:
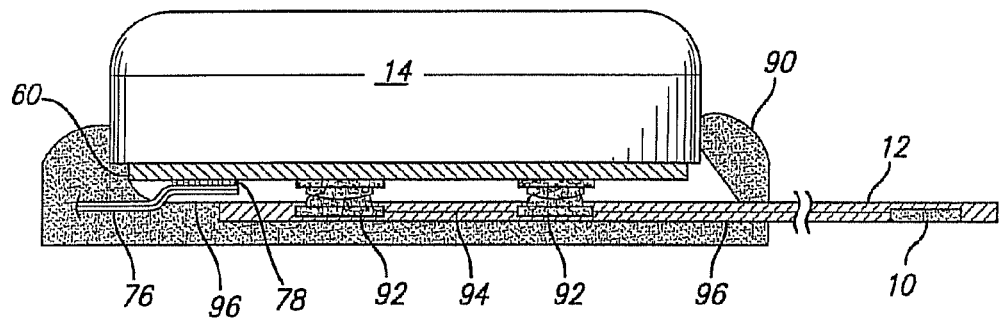
FIG. 7 is a view of the completed package attached to an electrode array.

FIG. 7 shows the flexible circuit 1, includes platinum conductors 94 insulated from each other and the external environment by a biocompatible dielectric polymer 96, preferably polyimide. One end of the array contains exposed electrode sites that are placed in close proximity to the retinal surface 10. The other end contains bond pads 92 that permit electrical connection to the electronics package 14. The electronic package 14 is attached to the flexible circuit 1 using a flip-chip bumping process, and epoxy underfilled. In the flip-chip bumping process, bumps containing conductive adhesive placed on bond pads 92 and bumps containing conductive adhesive placed on the electronic package 14 are aligned and melted to build a conductive connection between the bond pads 92 and the electronic package 14. Leads 76 for the secondary inductive coil 16 are attached to gold pads 78 on the ceramic substrate 60 using thermal compression bonding, and are then covered in epoxy. The electrode array cable 12 is laser welded to the assembly junction and underfilled with epoxy. The junction of the secondary inductive coil 16, array 1, and electronic package 14 are encapsulated with a silicone overmold 90 that connects them together mechanically. When assembled, the hermetic electronics package 14 sits about 3 mm away from the end of the secondary inductive coil.

Since the implant device is implanted just under the conjunctiva it is possible to irritate or even erode through the conjunctiva. Eroding through the conjunctiva leaves the body open to infection. We can do several things to lessen the likelihood of conjunctiva irritation or erosion. First, it is important to keep the over all thickness of the implant to a minimum. Even though it is advantageous to mount both the electronics package 14 and the secondary inductive coil 16 on the lateral side of the sclera, the electronics package 14 is mounted higher than, but not covering; the secondary inductive coil 16. In other words the thickness of the secondary inductive coil 16 and electronics package should not be cumulative.

It is also advantageous to place protective material between the implant device and the conjunctiva. This is particularly important at the scleratomy, where the thin film electrode cable 12 penetrates the sclera. The thin film electrode array cable 12 must penetrate the sclera through the pars plana, not the retina. The scleratomy is, therefore, the point where the device comes closest to the conjunctiva. The protective material can be provided as a flap attached to the implant device or a separate piece placed by the surgeon at the time of implantation. Further material over the scleratomy will promote healing and sealing of the scleratomy. Suitable materials include DACRON®, TEFLON®, GORETEX° (ePTFE), TUTOPLAST® (sterilized sclera), MERSILENE® (polyester) or silicone.

Figure 8:
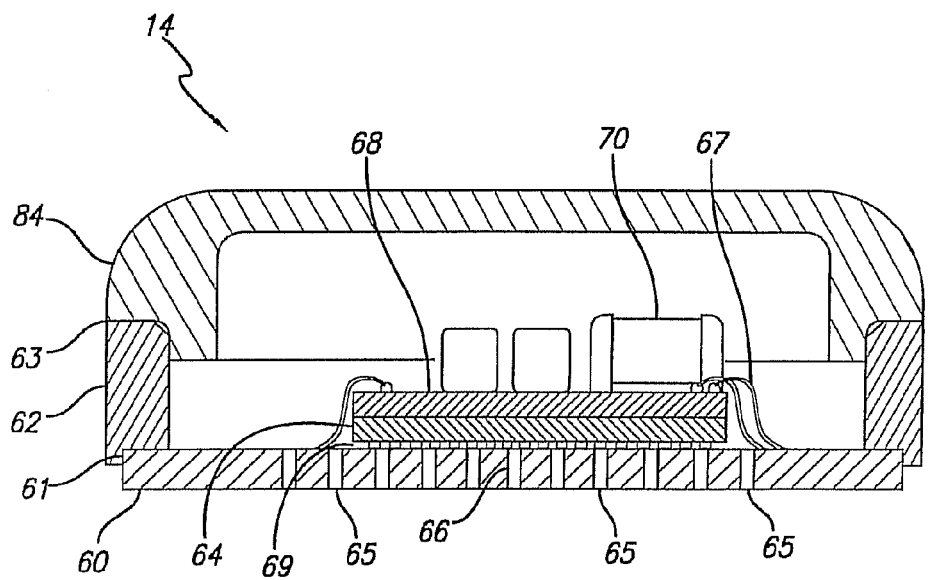
FIG. 8 is a cross-section of the package.

FIG. 8 shows the package 14 containing a ceramic substrate 60, with metallized vias 65 and thin-film metallization 66. The package 14 contains a metal case wall 62 which is connected to the ceramic substrate 60 by braze joint 61. On the ceramic substrate 60 an underfill 69 is applied. On the underfill 69 an integrated circuit chip 64 is positioned. On the integrated circuit chip 64 a ceramic hybrid substrate 68 is positioned. On the ceramic hybrid substrate 68 passives 70 are placed. Wirebonds 67 are leading from the ceramic substrate 60 to the ceramic hybrid substrate 68. A metal lid 84 is connected to the metal case wall 62 by laser welded joint 63 whereby the package 14 is sealed.

Figure 9:
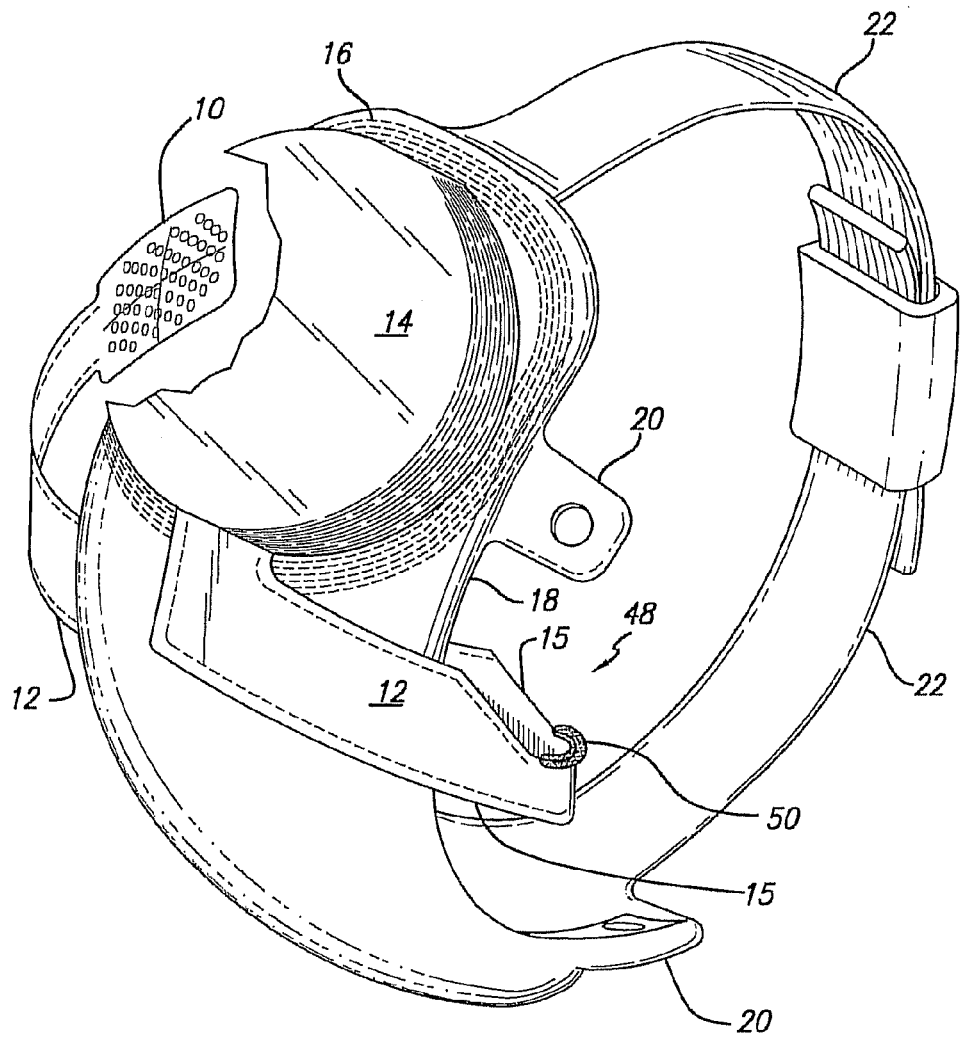
FIG. 9 is a perspective view of the implanted portion of the preferred retinal prosthesis.

FIG. 9 shows a perspective view of the implanted portion of the preferred retinal prosthesis which is an alternative to the retinal prosthesis shown in FIG. 1.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device.

Lid 84 and case wall 62 may also contain titanium or titanium alloy or other metals and metal alloys including platinum, palladium, gold, silver, ruthenium, or ruthenium oxide. Lid 84 and case wall 62 may also contain a polymer, copolymer or block copolymer or polymer mixtures or polymer multilayer containing parylene, polyimide, silicone, epoxy, or PEEK™ polymer. Via substrate may be preferably contain alumina or zirconia with platinum vias.

Figure 15:
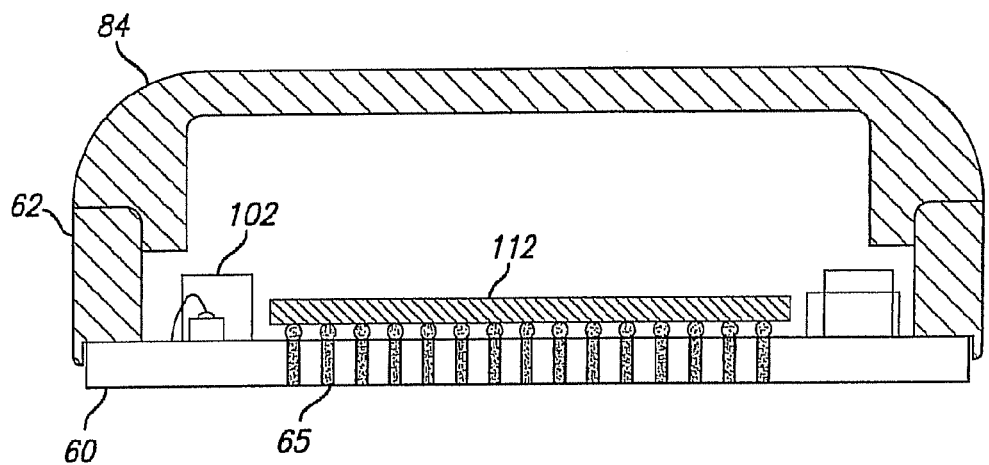
FIG. 15 is a cross-section of the one stack package.

FIG. 15 shows a one stack assembly. One stack means that all of the parts are on a flip chip integrated circuit 108, with or without a separate demux. A via substrate 60 is placed on the bottom below the flip chip IC 108 which includes RF transceiver, power recovery, drivers, and an optional demux. Discrete passives 102 are placed directly on the via substrate 60 to side of the flip chip IC 108.

Figure 12:
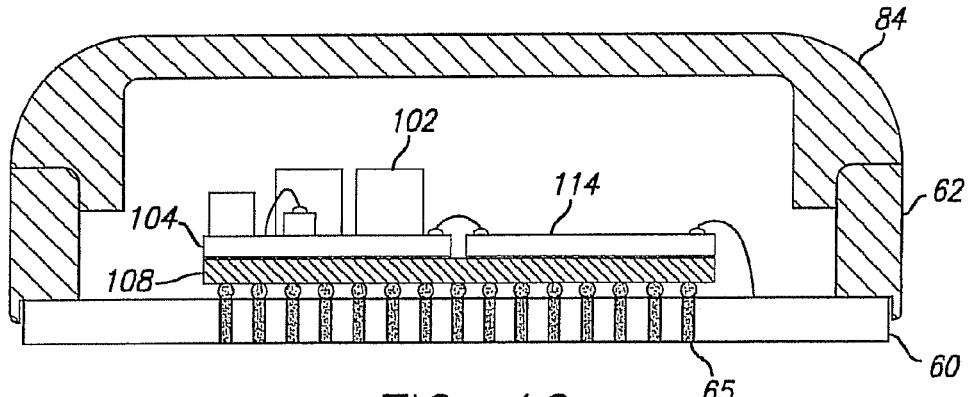
FIG. 12 is a cross-section of the two stack package.
Figure 13:
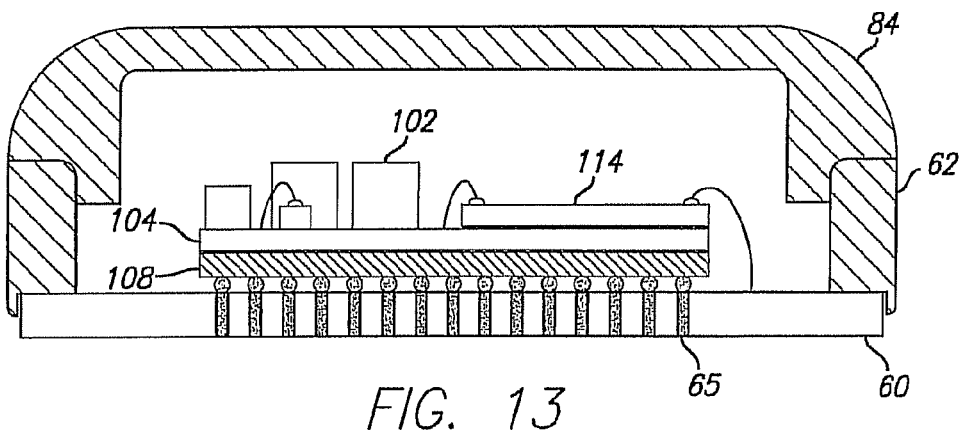
FIG. 13 is a cross-section of the two stack package.
Figure 14:
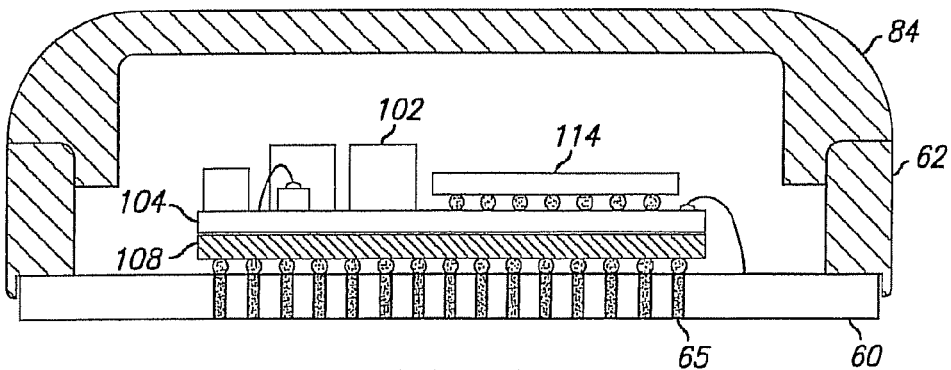
FIG. 14 is a cross-section of the two stack package.
Figure 16:
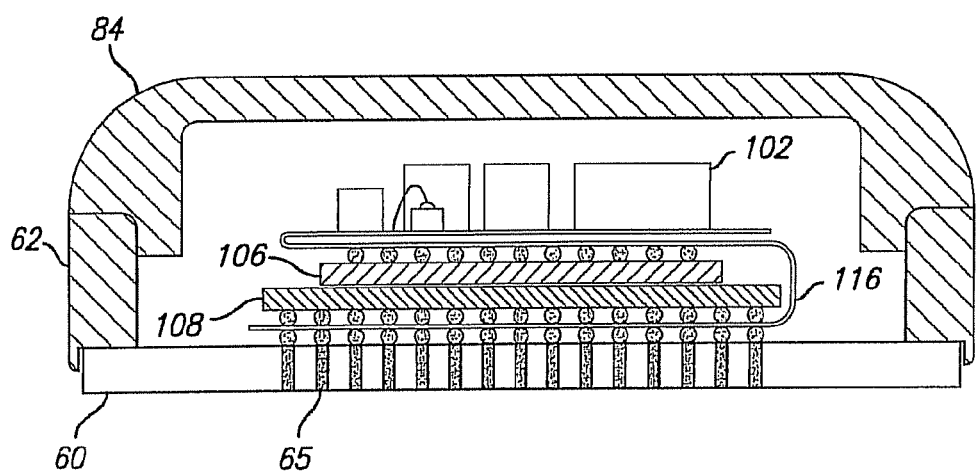
FIG. 16 is a cross-section of the folded stack package.

FIGS. 12, FIG. 13, and FIG. 14 show two stack assemblies. FIG. 16 shows a folded stack assembly. FIG. 12 shows a ceramic substrate 104 next to a RF transceiver/power recovery chip 114 and both placed on a flip chip driver/demux 108. FIG. 13 shows the ceramic substrate 104 on a flip chip driver/demux 108. The RF transceiver/power recovery chip 114 is provided on the ceramic substrate 104. FIG. 14 shows the ceramic substrate 104 on top of the flip chip driver/demux 108. The RF transceiver/power recovery chip 114 is provided not directly on the ceramic substrate 104. The difference between FIG. 13 and FIG. 14 is that in FIG. 13 the ceramic substrate 104 is in direct contact with RF transceiver/power recovery chip 114 but not in FIG. 14. The substrate 104 can be ceramic but also any kind of polymer or glass. FIG. 16 shows a folded stack substrate 116 with a flip chip demux 108 on the bottom and an IC 106 placed on the flip chip demux 108. The folded stack substrate 116 is folded twice.

Figure 10:
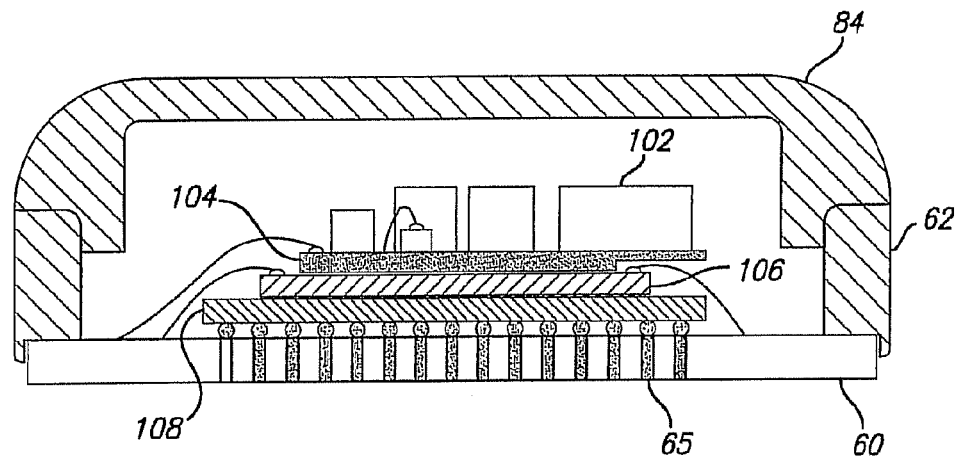
FIG. 10 is a cross-section of the three stack package.
Figure 11:
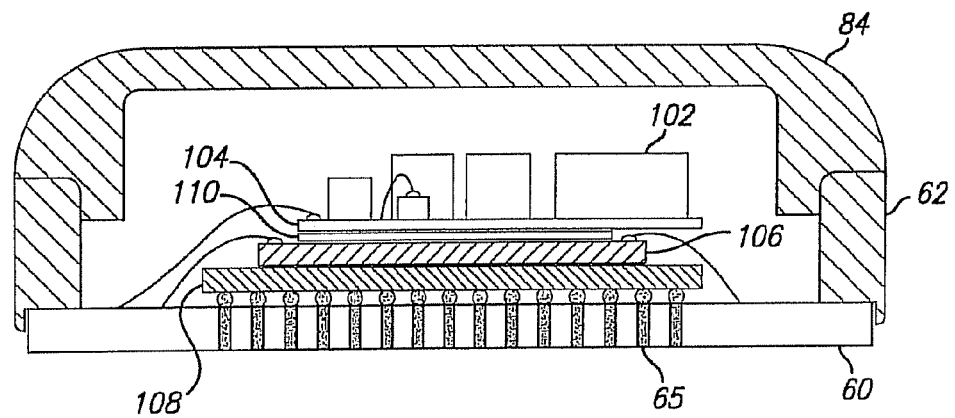
FIG. 11 is a cross-section of the three stack package.

FIG. 10 and FIG. 11 show a three stack assembly. A three stack assembly with a demux flip chip 108 bonded to via substrate 60. Preferably, an IC 106 and hybrid ceramic substrate 104 are on top of flip chip 108, each wire-bonded to via substrate 60. FIG. 10 shows hybrid ceramic substrate 104 on an IC 106 including RF transceiver, power recovery, and drivers and the IC 106 is placed on a flip chip demux 108. FIG. 11 shows a similar assembly as FIG. 10 however the hybrid ceramic substrate 104 is placed on a pedestal 110 which is placed between the substrate 104 and the IC 106.

Figure 17:
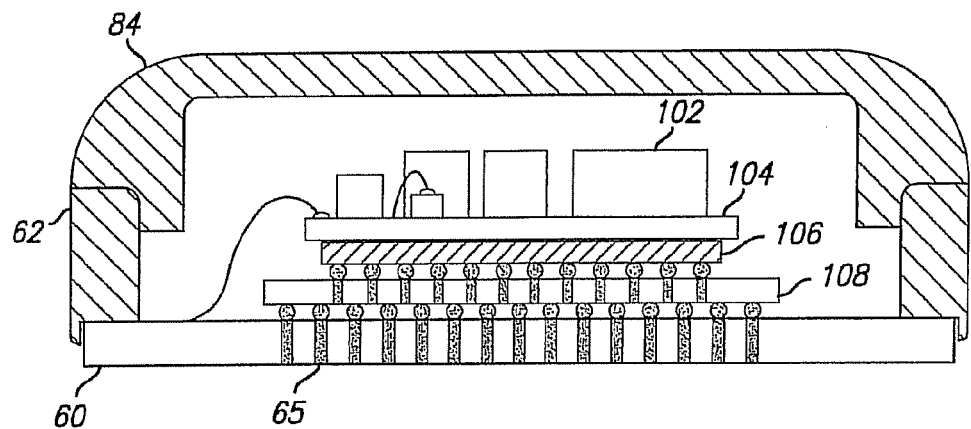
FIG. 17 is a cross-section of the package.
Figure 18:
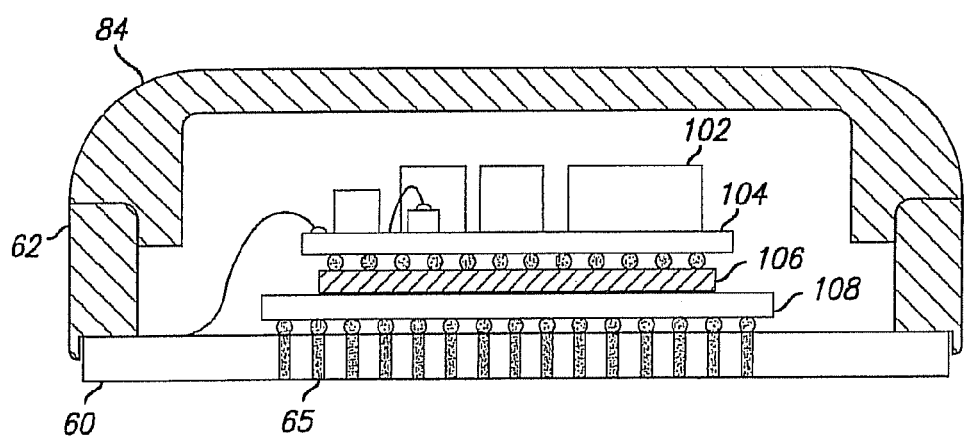
FIG. 18 is a cross-section of the package.

FIG. 17 and FIG. 18 show additional flip chip configurations. Both figures have a similar assembly. However, in FIG. 17 the IC 106 is bonded to the flip chip demux 108 by a bump bond. In FIG. 18 a double sided, multilayer ceramic substrate 104 is bonded to the IC 106 by a bump bond.

The assembly can include two stacks or a folded stack. Each stack could be one or two-sided. There may be passives 102 on the hybrid ceramic substrate. A pedestal is useful but optional to make room for wire bonds. A bump bond to the IC and then a bump bond to the IC to the passive substrate or demux is possible. Bond pads on the IC to line up with vias to eliminate the inside metallization can be provided. The IC flip chip with drivers can be bonded to the hybrid ceramic substrate. The demux flip chip can be bonded to the via substrate, and the two substrates (i.e. the via substrate and hybrid substrate) can be wire-bonded or flex circuit bonded together. The driver portion can be moved to a demux chip and everything else to a separate chip to reduce interconnect lines. A two stack assembly can be provided with a smaller chip (with RF and demux) and hybrid ceramic substrate above. It may include wire bonds directly from the hybrid ceramic substrate to the smaller chip.

Figure 19:
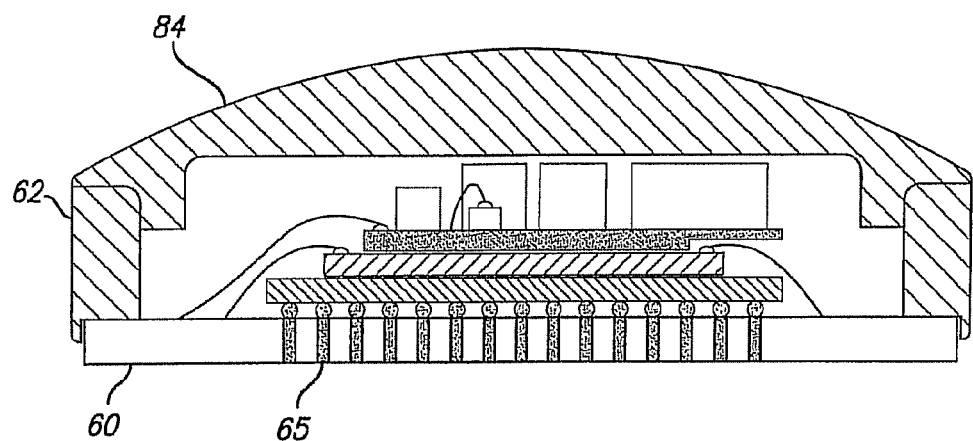
FIG. 19 is a cross-section of the lid shaping package.
Figure 20:
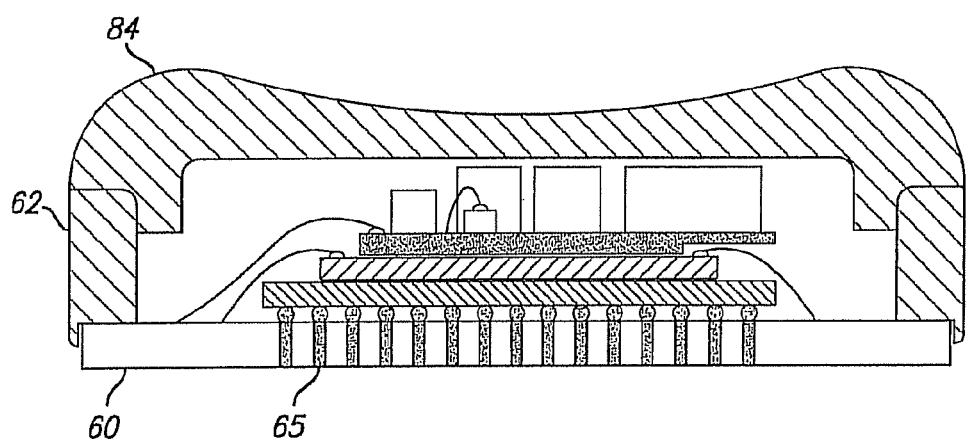
FIG. 20 is a cross-section of the lid shaping package.

FIG. 19 and FIG. 20 show different variations of the lid shape. It is possible to have a convex or concave lid 84 to conform to eye.

Figure 21:
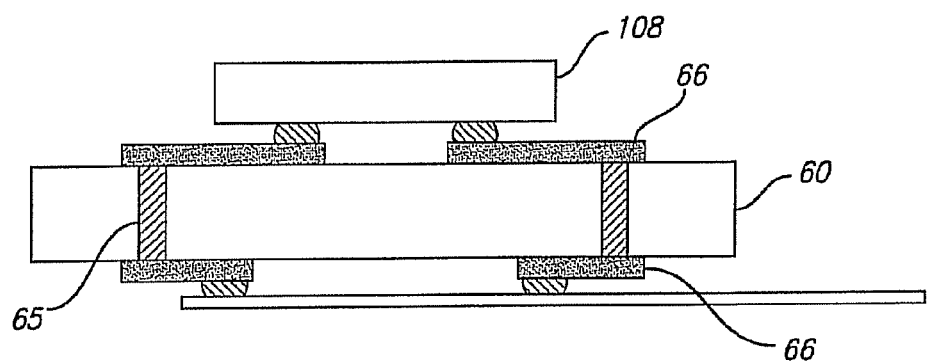
FIGS. 21 and 22 are cross-sections the package showing interconnects in detail.
Figure 22:
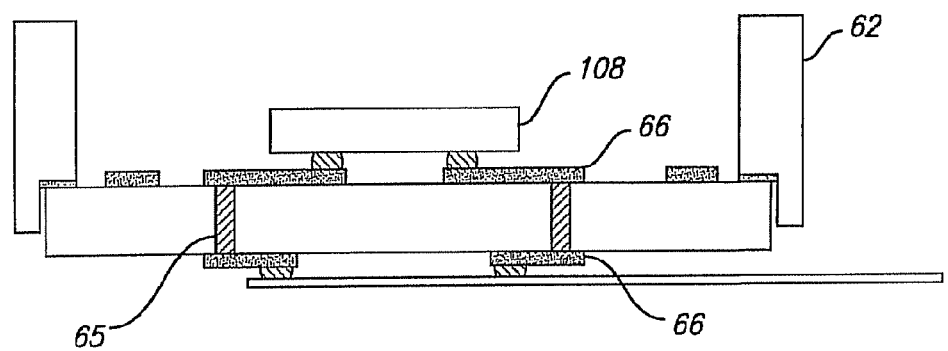

FIG. 21 and FIG. 22 are cross-sections of the package showing redistribution routing and interconnect traces 66 in detail. Both figures show redistribution routings and interconnect traces 66 on the top and the bottom of the via substrate 60. Redistribution routing 66 on top of the via substrate 60 and a braze stop 120 on top of the via substrate 60 contain preferably metals such as Ti, Zr, Fe, Ru, Co, Rh, Ir, Ni, Pd, Pt, Cu, Ag, Au, mixtures, layers or alloys thereof. The top layer of the top redistribution routing is gold or gold alloy. Redistribution routing 66 on bottom of the via substrate 60 and the braze stop 120 on top of the via substrate 60 contain preferably metals like Ti, Zr, Fe, Ru, Co, Rh, Ir, Ni, Pd, Pt, Cu, Ag, Au, mixtures, layers or alloys thereof. The top layer of the top redistribution routing is platinum or platinum alloy. Interconnect and redistribution routing 66 facilitates the electrical connection between flexible circuit 12 and via substrate 60 on the bottom of the substrate and between the flip chip circuit 64 and the via substrate 60 on top of the substrate. Additional braze stop traces 120 surround the redistribution and interconnect traces 66 to prevent the braze metal 122 from running into the redistribution and interconnect traces 66. The walls 62 in FIG. 22 show the same braze metal 122 as mentioned before as a flange.

Accordingly, what has been shown is an improved method for making a hermetic package for implantation in a body. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What we claim is:

1. An implantable device comprising:
an electrically non-conductive substrate;
a plurality of electrically conductive vias through said electrically non-conductive substrate;
a plurality of metal traces on said electrically non-conductive substrate electrically connected to said conductive vias;
a braze stop on said electrically non-conductive substrate and along a periphery of said non-conductive substrate surrounding said plurality of metal traces, and separating a braze joint from said plurality of metal traces;
said electrically non-conductive substrate, said traces, said braze stop trace, and said electrically conductive vias forming a base; a flip-chip circuit attached directly to said base using conductive bumps;
a second circuit attached directly to said base; and
a cover brazed to said base at said braze joint, said cover, and said base forming a hermetic package;
wherein said flip-chip circuit and said second circuit are adjacent to each other, and mounted to a common substantially planar surface of said base and said braze stop trace prevents said braze from contacting said metal traces.

2. The implantable device according to claim 1, wherein said electrically conductive vias are a metallic and ceramic paste co-fired with said electrically non-conductive substrate to form a hermetic seal.

3. The implantable device according to claim 1, wherein said metal traces are chosen to withstand braze temperatures.

4. The implantable device according to claim 3, wherein said metal traces comprise one or more of the metals titanium, tantalum, gold, palladium, platinum or layers or alloys thereof.

5. The implantable device according to claim 1, further comprising a flexible circuit bump bonded to said base.

6. The implantable device according to claim 5, wherein said flexible circuit is an electrode array suitable for stimulating tissue.

7. The implantable device according to claim 1, further comprising a polymer underfill under said flip-chip circuit.

8. The implantable device according to claim 1, wherein said conductive bumps contain at least one conductive polymer.

9. The implantable device according to claim 1, wherein said conductive bumps contain at least one conductive epoxy or polyimide.

10. The implantable device according to claim 1, wherein said conductive bumps are filled with one or more metals like from the group including silver, platinum, iridium, titanium, platinum alloys, iridium alloys, or titanium alloys or mixtures thereof.

11. The implantable device according to claim 10, wherein said metal or metal alloys are in dust, flake or powder form.

12. The implantable device according to claim 1, wherein said flip chip circuit contains one or two stacks.

13. The implantable device according to claim 1, wherein said flip chip circuit contains three stacks.

* * * * *